(12) United States Patent
Wei

(10) Patent No.: US 8,426,463 B2
(45) Date of Patent: Apr. 23, 2013

(54) [((1R,2S,5R)-2-ISOPROPYL-5-METHYL-CYCLOHEXANECARBONYL)-AMINO]-ACETIC ACID ISOPROPYL ESTER AND RELATED COMPOUNDS AND THEIR USE IN THERAPY

(76) Inventor: Edward T. Wei, Berkeley, CA (US)

(*) Notice: Subject to any disclaimer, the term of this patent is extended or adjusted under 35 U.S.C. 154(b) by 0 days.

(21) Appl. No.: 13/065,971

(22) Filed: Apr. 4, 2011

(65) Prior Publication Data
US 2012/0251461 A1    Oct. 4, 2012

(51) Int. Cl.
*A61K 31/223* (2006.01)
*A61K 31/196* (2006.01)
*A61K 9/20* (2006.01)
*A61K 9/68* (2006.01)
*A61P 11/02* (2006.01)
*A61P 11/04* (2006.01)

(52) U.S. Cl.
USPC ............ 514/506; 424/48; 424/465; 424/435; 514/616; 560/1

(58) Field of Classification Search ............... None
See application file for complete search history.

(56) References Cited

U.S. PATENT DOCUMENTS

| | | | | |
|---|---|---|---|---|
| 4,136,163 | A * | 1/1979 | Watson et al. ................. | 424/54 |
| 2005/0137166 | A1* | 6/2005 | Asgharian et al. ............ | 514/54 |
| 2008/0227857 | A1* | 9/2008 | Wei ................................ | 514/473 |

FOREIGN PATENT DOCUMENTS

| WO | WO 2006103401 A2 | * | 10/2006 |
|---|---|---|---|
| WO | WO 2009027331 A2 | * | 3/2009 |

* cited by examiner

*Primary Examiner* — Frederick Krass
*Assistant Examiner* — Michael P Cohen

(57) ABSTRACT

The present invention pertains generally to the field of coolants and medical therapy. More particularly, the present invention relates to certain anti-nociceptive agents, such as [((1R,2S,5R)-2-isopropyl-5-methyl-cyclohexanecarbonyl)-amino]-acetic acid isopropyl ester, that are potent and long-acting and selectively cooling for non-keratinized epithelial tissues as compared to keratinized epithelial tissues, and are useful, for example, for the treatment of (e.g., the alleviation of symptoms of; the amelioration of) sensory discomfort of non-keratinized stratified epithelial (NKSE) tissue; and so for treatment of: sensory discomfort of an ocular surface, an eyelid, a margin of an eyelid, an anterior part of an eyeball, a conjunctiva, a lachrymal system, a pre-corneal film, or a cornea, a lining of the oral cavity, an internal portion of the lips, a pharyngeal surface, an esophageal surface, or an anogenital surface; eye discomfort, e.g., caused by extended wear of contact lenses, by eye strain and/or fatigue, by air pollutants, by excessive exposure to the sun, by conjunctivitis, by dry eye syndrome; sensory discomfort associated with oral mucositis; airway (e.g., larynx, trachea, and/or bronchi) tightness, discomfort in the airways (e.g., larynx, trachea, and/or bronchi), choking, cough, and/or dyspnea, e.g., associated with asthma and/or chronic obstructive pulmonary diseases (COPD).

4 Claims, No Drawings

[((1R,2S,5R)-2-ISOPROPYL-5-METHYL-CYCLOHEXANECARBONYL)-AMINO]-ACETIC ACID ISOPROPYL ESTER AND RELATED COMPOUNDS AND THEIR USE IN THERAPY

TECHNICAL FIELD

The present invention pertains generally to the field of medical therapy. More particularly, the present invention relates to certain anti-nociceptive agents, such as [((1R,2S,5R)-2-isopropyl-5-methyl-cyclohexanecarbonyl)-amino]-acetic acid isopropyl ester, that are potent and long-acting and selectively cooling for non-keratinized epithelial tissues as compared to keratinized epithelial tissues, and are useful, for example, for the treatment of (e.g., the alleviation of symptoms of; the amelioration of) sensory discomfort of non-keratinized stratified epithelial (NKSE) tissue; and so for treatment of: sensory discomfort of an ocular surface, an eyelid, a margin of an eyelid, an anterior part of an eyeball, a conjunctiva, a lachrymal system, a pre-corneal film, or a cornea, a lining of the oral cavity, an internal portion of the lips, a pharyngeal surface, an esophageal surface, or an anogenital surface; eye discomfort, e.g., caused by extended wear of contact lenses, by eye strain and/or fatigue, by air pollutants, by excessive exposure to the sun, by conjunctivitis, by dry eye syndrome; sensory discomfort associated with oral mucositis; airway (e.g., larynx, trachea, and/or bronchi) tightness, discomfort in the airways (e.g., larynx, trachea, and/or bronchi), choking, cough, and/or dyspnea, e.g., associated with asthma and/or chronic obstructive pulmonary diseases (COPD).

BACKGROUND OF THE INVENTION

A number of publications are cited herein in order to more fully describe and disclose the invention and the state of the art to which the invention pertains. Each of these references is incorporated herein by reference in its entirety into the present disclosure, to the same extent as if each individual reference was specifically and individually indicated to be incorporated by reference.

Throughout this specification, including the claims which follow, unless the context requires otherwise, the word "comprise," and variations such as "comprises" and "comprising," will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Thus, for example, reference to "a pharmaceutical carrier" includes mixtures of two or more such carriers, and the like.

Ranges are often expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment.

This disclosure includes information that may be useful in understanding the present invention. It is not an admission that any of the information provided herein is prior art or relevant to the presently claimed invention, or that any publication specifically or implicitly referenced is prior art.
Nociception Nociception may be defined as the neural processes of encoding and processing noxious stimuli. Of particular interest are anti-nociceptive drugs that act peripherally. By "anti-nociceptive", it is meant that the drug suppresses the psychical and physiological perception of noxious stimuli. By "peripherally", it is meant that the primary site of the drug action is located outside the central nervous system, that is, outside of the brain and spinal cord.

There are currently two major classes of anti-nociceptive drugs that act peripherally to attenuate transmission of nociceptive (noxious) signals to the central nervous system. One class is local anesthetics, such as procaine and lidocaine, which act on peripheral nerve fibers to inhibit nerve conduction of nociceptive signals towards the central nervous system.

Another class is agents such as aspirin and ibuprofen that inhibit the synthesis of certain prostaglandins. These prostaglandins, when released by tissues during injury or inflammation, lower the threshold for firing of sensory nerve fibers that respond to noxious stimuli. Yet another class of anti-nociceptive drugs is the narcotic analgesics, which do not suppress pain via peripheral actions but instead act directly on neuronal elements in the brain and spinal cord.

Pain, defined by Sir Charles Sherrington as "the psychical adjunct of an imperative protective reflex", is activated by increased discharge of unmyelinated small-diameter sensory fibers called polymodal C fibers. Pain is categorized as nociceptive or neuropathic. Nociceptive pain is caused by cell injury and neuropathic pain is caused by damage to the nerve fibers that transmit the pain signals. There are many conditions that produce pain; the most common being, for example, trauma, inflammation, and immune disorders. Sensations that may accompany pain are irritation, pruritus (itch), and a sense of malaise and disaffection. As used herein, the psychical adjuncts of nociception are together categorized as "sensory discomfort".

There are four basic types of animal tissues: connective tissue, muscle tissue, nervous tissue and epithelial tissue. Epithelial cells line cavities and surfaces of organs throughout the body. When the layer is one cell thick, it is called simple epithelium. If there are two or more layers of cells, it is called stratified epithelium. Stratified epithelium is composed mainly of squamous (flattened) cells and some cuboidal cells. In the skin, external lip, and tongue, the exterior layer of cells of stratified epithelium are dead and become a tough, water-impermeable protein called keratin. Stratified squamous epithelia which do not contain keratin are present on the ocular surfaces including the margin of the eyelid, the anterior part of the eyeball, the conjunctiva, the lachrymal system, the pre-corneal film, and the cornea; the lining of the oral cavity including the internal portion of the lips; the pharyngeal surface; the esophageal surface; and the anogenital surface. Keratinized tissues withstand injury better than non-keratinized tissues. Non-keratinized epithelial surfaces must be kept moist by glandular (serous and mucous) secretions in order to prevent desiccation.

Current topical anti-nociceptive (pain-suppressant) compounds have limited efficacy on pain from non-keratinized stratified epithelium (NKSE). This is especially true for sensory discomfort from the ocular surfaces.

Local anesthetic compounds such as lidocaine are used for pain and discomfort from anogenital surfaces (e.g., for vulvovaginal pain) and from the pharynx (e.g., for cough and pharyngitis) but these drugs can cause hypersensitivity reactions and have the undesirable property of numbing the tissues to touch and pressure. Local anesthetics can be used in an emergency for pain from the ocular surfaces, especially corneal pain, but prolonged use is dangerous because this class of drugs inhibits epithelial cell growth.

The non-steroidal anti-inflammatory compounds (NSAIDs), for example, ketorolac, can be used on the ocular surface for a short period time, for example, to reduce the acute pain of cataract surgery, but not for prolonged use on the eye. Topical NSAIDs do not work for pain arising from anogenital or oral cavity NKSE.

Menthol has some limited analgesic action in ointments for hemorrhoidal discomfort. In lozenges and confectionery, menthol has some benefit for sore or irritated throats and for cough. Menthol is highly irritating to the eyes but is used in some eye drops in Japan. On keratinized skin, high concentrations of menthol (for example, more than 2% by weight) can be applied without direct irritation to the skin. For example, topical patches containing 5% by weight menthol (e.g., IcyHot Medicated Patch; Chattem, Inc.) can be applied onto the skin of the torso to relieve muscular pain. On non-keratinized epithelia, however, the irritating effects of menthol limit its use; for example, lozenges containing more than 8 mg of menthol per unit are aversive in taste.

There is a need for a new class of pharmacological agent that can suppress sensory discomfort arising from NKSE but without the problems of irritancy and toxicity.

Watson et at, "Compounds with the Menthol Cooling Effect", *J. Soc. Cosmet. Chem.*, Vol. 29, pp. 185-200, 1978, describes a number of compounds with physiological cooling effects on keratinized epithelia such as the skin and the tongue. The studies described therein provide a background for the discovery of other compounds with more selective actions on NKSE.

Watson et al., 1979, "N-Substituted paramenthane carboxamides", U.S. Pat. No. 4,178,459 granted 11 Dec. 1979. describes "N-substituted paramenthane carboxamides" of the following formula. Among the examples therein are compounds where R' is —H and R" is —CH$_2$C(═O)OCH$_3$, —CH$_2$C(═O)OCH$_2$CH$_3$, or —CH$_2$C(═O)OCH$_2$CH$_2$CH$_3$. The corresponding compound where R" is —CH$_2$C(═O)OCH(CH$_3$)$_2$ is not shown.

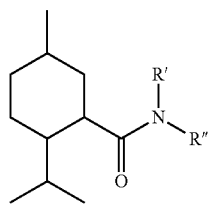

SUMMARY OF THE INVENTION

One aspect of the invention pertains to an IPE compound, as described herein.

Another aspect of the invention pertains to a composition comprising an IPE compound, as described herein.

Another aspect of the invention pertains to an IPE compound, as described herein, for treatment of the human or animal body by therapy.

Another aspect of the invention pertains to an IPE compound, as described herein, for treatment of sensory discomfort in a human, as described herein.

Another aspect of the invention pertains to a method of treatment of sensory discomfort in a human, as described herein, comprising administration of a therapeutically effective amount of the IPE compound, as described herein.

Another aspect of the invention pertains to use of an IPE compound, as described herein, in the manufacture of a medicament for the treatment of sensory discomfort in a human, as described herein.

As will be appreciated by one of skill in the art, features and preferred embodiments of one aspect of the invention will also pertain to other aspects of the invention.

DETAILED DESCRIPTION

Compounds

The inventor has discovered that certain compounds are surprisingly and unexpectedly effective cooling agents for non-keratinized stratified epithelium (NKSE) tissue. These compounds are potent and long-acting and selectively cooling for non-keratinized epithelial tissues as compared to keratinized epithelial tissues.

These compounds are collectively referred to herein as "Isopropyl Ester Compounds" or "IPE Compounds", and are:

[((1R,2S,5R)-2-isopropyl-5-methyl-cyclohexanecarbonyl)-amino]-acetic acid isopropyl ester ("Gly-O-iPr") and

[((1R,2S,5R)-2-isopropyl-5-methyl-cyclohexanecarbonyl)-methyl-amino]-acetic acid isopropyl ester ("N-Gly-O-iPr");

and pharmaceutically acceptable salts, hydrates, and solvates thereof.

Thus, one aspect of the invention is a compound which is:

[((1R,2S,5R)-2-isopropyl-5-methyl-cyclohexanecarbonyl)-amino]-acetic acid isopropyl ester ("Gly-O-iPr"), or

[((1R,2S,5R)-2-isopropyl-5-methyl-cyclohexanecarbonyl)-methyl-amino]-acetic acid isopropyl ester ("N-Gly-O-iPr");

or a pharmaceutically acceptable salt, hydrate, or solvate thereof.

The compounds Gly-O-iPr and N-Gly-O-iPr are illustrated in the following table.

| Code Name | Chemical Name | Chemical Structure |
| --- | --- | --- |
| Gly-O—iPr | [((1R,2S,5R)-2-isopropyl-5-methyl-cyclohexanecarbonyl)-amino]-acetic acid isopropyl ester | 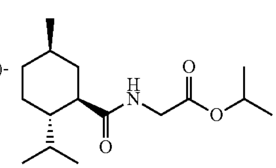 |
| N-Gly-O—iPr | [((1R,2S,5R)-2-isopropyl-5-methyl-cyclohexanecarbonyl)-methyl-amino]-acetic acid isopropyl ester | 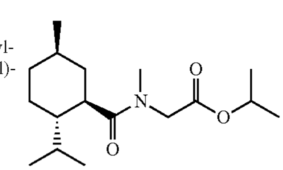 |

These compounds are structurally related to (−)-menthol, and have the same chiral centres, in the same configuration, as those found in (−)-menthol.

| Name | Chemical Name | Chemical Structure |
|---|---|---|
| (−)-menthol | (1R,2S,5R)-2-isopropyl-5-methyl-cyclohexanol | 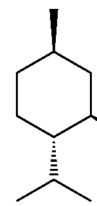 |

In structural terms, the compounds may conveniently be described as the isopropyl ester of the glycine amide and the N-methyl-glycine amide, respectively, of the carboxylic acid corresponding to (−)-menthol.

In one embodiment, the compound is [((1R,2S,5R)-2-isopropyl-5-methyl-cyclohexanecarbonyl)-amino]-acetic acid isopropyl ester or a pharmaceutically acceptable salt, hydrate, or solvate thereof.

In one embodiment, the compound is [((1R,2S,5R)-2-isopropyl-5-methyl-cyclohexanecarbonyl)-amino]-acetic acid isopropyl ester or a pharmaceutically acceptable salt thereof.

In one embodiment, the compound is [((1R,2S,5R)-2-isopropyl-5-methyl-cyclohexanecarbonyl)-amino]-acetic acid isopropyl ester.

Chemical Synthesis

In one approach, alkyl esters of the glycine amide of the carboxylic acid corresponding to (−)-menthol may be prepared by reacting the acid halide (e.g., the acid chloride) of the carboxylic acid corresponding to (−)-menthol with the appropriate glycine alkyl ester, for example, as illustrated below.

Scheme 1

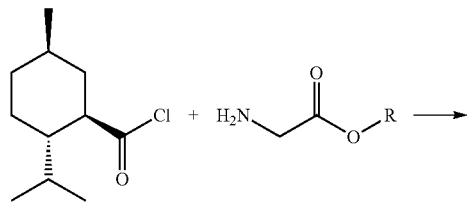

Many glycine alkyl esters (including methyl and ethyl glycine esters) are commercially available, for example, from Sigma-Aldrich. Other glycine alkyl esters may be prepared by those of ordinary skill in the art using known and/or conventional methods.

For example, the ethyl ester compound (where R is Et), referred to herein as Gly-O-Et, was prepared as follows: 1.0 g of glycine ethyl ester hydrochloride (Sigma-Aldrich) was dissolved in 28 mL diethyether and 1 mL double-distilled water and cooled to 0° C. A pinch of the catalyst diaminopyrimidine was added. 1.62 mL of p-menthoyl chloride was added dropwise, followed by 2 mL of triethylamine. Clumps of white precipitate appeared in the mixture, which was stirred overnight at room temperature. The precipitate was collected, dissolved in ethyl acetate, washed with double-distilled water, and dried over sodium sulfate. The organic phase was then evaporated under reduced pressure to yield the final product (2 g), which crystallized at room temperature. High-performance liquid chromatography (HPLC) revealed a single peak accounting for more that 95% of the material. Mass spectroscopy (MS) and nuclear magnetic resonance (NMR) was used to confirm its identity.

The isopropyl compound (where R is iPr), referred to herein as Gly-O-iPr, was prepared by Phoenix Pharmaceuticals, Burlingame, Calif. (www.phoenixpeptide.com): Lot No. 427497; $C_{16}H_{29}NO_3$; molecular weight 283.41; purity≧95% by weight; appearance: white crystalline powder. Additional compounds were prepared by Diapharm Ltd., St. Petersburg, Russia.

The following compounds were prepared.

| # | Code | Chemical Name | Chemical Structure |
|---|---|---|---|
| 1 | Gly-O—Me | [((1R,2S,5R)-2-isopropyl-5-methyl-cyclohexanecarbonyl)-amino]-acetic acid methyl ester | 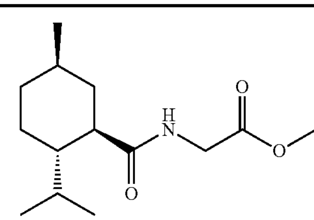 |
| 2 | Gly-O—Et | [((1R,2S,5R)-2-isopropyl-5-methyl-cyclohexanecarbonyl)-amino]-acetic acid ethyl ester | 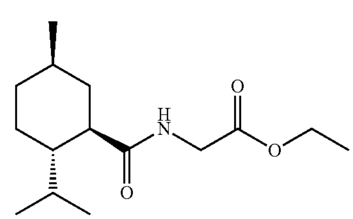 [SMILES: CCOC(=O)CNC(=O)[C@@H]1C[C@H](C)CC[C@H]1C(C)C] |

-continued

| # | Code | Chemical Name | Chemical Structure |
|---|---|---|---|
| 3 | Gly-O—nPr | [((1R,2S,5R)-2-isopropyl-5-methyl-cyclohexanecarbonyl)-amino]-acetic acid n-propyl ester | 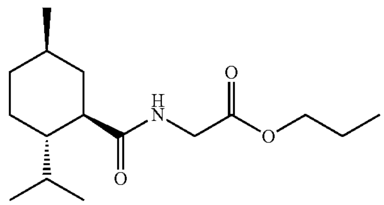 [SMILES: CCCOC(=O)CNC(=O)[C@@H]1C[C@H](C)CC[C@H]1C(C)C] |
| 4 | Gly-O—iPr | [((1R,2S,5R)-2-isopropyl-5-methyl-cyclohexanecarbonyl)-amino]-acetic acid isopropyl ester | 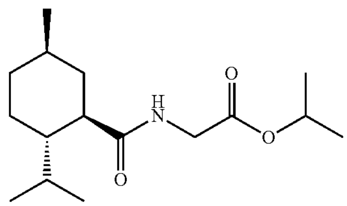 [SMILES: CC(C)OC(=O)CNC(=O)[C@@H]1C[C@H](C)CC[C@H]1C(C)C] |
| 5 | Gly-O—nBu | [((1R,2S,5R)-2-isopropyl-5-methyl-cyclohexanecarbonyl)-amino]-acetic acid n-butyl ester | 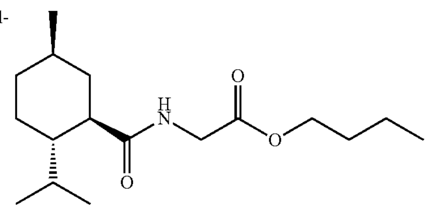 |

Biological Evaluation

Chemicals that evoke cooling thermosensations have several observable properties when tested in human subjects. Firstly, there is the sensation itself; for example, the subject may be asked: does it feel mildly cool, cool, or cold? Secondly, there is the intensity of the sensation; for example, the subject may be asked: is it refreshing cool, robust cool, intense cold, or burning cold? Thirdly, there is duration of action; the subject may be asked: how long does the effect last? The duration of action is typically measured by the onset and offset of the sensation, and is usually minutes or a few hours. Fourthly, there is potency; the potency of a specific test compound for eliciting cooling is typically reported using the applied concentration (e.g., % by weight; mg/mL; etc.) or the dosage (e.g., mg per unit body weight).

Bioassay on Keratinized Stratified Epithelium: Philtrum Assay

The philtrum is the midline groove above the border of the upper lip. The site of drug testing was the skin above the upper lip (above the vermilion border of the lips), on the philtrum, lateral to the philtrum until the nasolabial folds, and sometimes on the lower nostrils (subnasale). This part of the face is known to be densely innervated with cool/cold receptors, second only to the surfaces of the eyeball and anogenitalia. It is also known from the scientific literature that the area around the lips has a high density of "cold spots" (see, e.g., Dhaka et al., "Visualizing cold spots: TRPM8-expressing sensory neurons and their projections", *J. Neuroscience*, Vol. 28, pp. 566-575, 2008).

To test for anti-nociceptive activity, the test substance is first dissolved (5 mg/mL) in an ointment (Aquaphor®), which is 41% petrolatum, and the rest mineral oil, ceresin and lanolin alcohol) and singly applied (40 to 70 mg) onto the philtrum skin surface using a plastic stick.

At this locus, cool and cold sensations in the skin may be experienced and rated for time of onset and intensity. The intensity of the subjective skin sensation is rated as 0, 1, 2 or 3 with: 0 as no change; 1 as slight coolness, or cold; 2 as clear-cut signal of coolness or cold; and 3 as robust cooling or cold. The intervals for recording are 5 to 10 minutes, until two successive zeroes are obtained. The onset of drug action is taken as the time to reach 2 units of coolness intensity, and offset of drug action is the time when coolness intensity drops below 2, after previously surpassing 2 units. The duration of cooling action is defined as the offset time minus the onset time. An inactive compound is defined as one that does not exceed 2 units of cooling for 5 minutes at any time after application.

Watson et al., 1979 describes testing of the properties of N-substituted p-menthane carboxamides on volunteers by putting filter paper (1×1 cm), impregnated with a known amount of test compound, onto the dorsal surface of the tongue of the test subject. After 30 seconds, the subject was required to report presence or absence of a cooling effect. These data were reported as "Threshold, μg" and refer to the threshold amount of the test compound that produced cooling sensations upon application onto the tongue of a panel of human volunteers. The average threshold for (−)-menthol for 6 subjects was 0.25 μg, but there was a 100-fold variation in individual sensitivity. The dorsal surface of the tongue is keratinized. Keratin is a component of finger-like projections called papillae which are in charge of the sense of taste. Coolness signals detected using the method of described in Watson et al., 1979, may not reflect drug actions on NKSE.

Bioassay on Non-Keratinized Stratified Epithelium: Ocular Surface

For testing on the ocular surface, a towelette containing the test compound was used as the delivery unit. The test compound was dissolved first in absolute ethanol and then distilled water was added to form a standard 1 mg/mL solution in a 3 to 5% by weight ethanol-water solution. Three mL of the test solution was then added to a 0.4 g cotton rectangle (50 mm×60 mm) (CS-being, Daisan Cotton, Japan) and individually sealed with a vacuum apparatus (Foodsaver®, Jarden Corp.). Samples were stored in a freezer or refrigerator and thawed to room temperature before use. Wiping with the cotton pad delivers 40 to 45 µL of liquid composition to the closed eyelids (~20 to 22 µL per eye surface). Thus, if the concentration of the test compound was 1 mg/mL, the dose delivered to both eyes is a total of ~40 to 42 µg, or ~20 µg per eye. The presence or absence of cooling sensations felt on the ocular surface was noted as being present or absent at 5 to 10 minute intervals until no coolness was noticeable in two successive test intervals. Only the duration of cooling on the ocular surface was recorded, without an attempt to quantify the intensity of the sensation.

Bioassay on Non-Keratinized Stratified Epithelium: Oropharyngeal Surface

A number of irritants have been evaluated for evoking the cough sensation as a measure of pharygeal sensitivity (see, e.g., Morice et al., 2001, "Cough Challenge in the Assessment of Cough Reflex", *Brit. J. Clin. Pharmacol.*, Vol. 52, pp. 365-375). Usually, citric acid or capsaicin is delivered via the inhalation route to volunteers and the number of coughs counted. The inventor has found that the sensations in the lower pharynx associated with the urge to clear the throat can be replicated by placing (with a syringe or a plastic stick) 0.2 to 0.25 mL of a chili pepper sauce onto the posterior dorsal surface of the tongue. The chili pepper sauce mixes with the saliva and the saliva is then deposited on the posterior oropharynx. The chili pepper sauce used was Yank Sing® Chili Pepper Sauce (YS Gourmet Productions, Inc., PO Box 26189, San Francisco, Calif. 94126) and is a well-known condiment for use with dim sum (Chinese tea lunch). The sensations associated with the chili pepper sauce are located in the posterior wall of the mouth and are clearly recognized by the test subject and associated with a desire to clear the throat. The chili-pepper sauce evoked sensations can be readily suppressed by drinking ice-cold water or using an orally disintegrating tablet (ODD containing a cooling ingredient, but is not affected by an ODT containing only the excipient.

The ODT was formulated by taking an ingredient, dissolving it in absolute ethanol, and then adding 10% by weight of maltitol, and 90% by weight of mannitol, and then an equal volume of distilled water. The mixture was the stirred with a glass rod, and dispensed onto a piece of wax paper with a disposable plastic pipette. The individual dried tablets weighed on average 150 mg each and when on the dorsal surface of the tongue, dissolved completely in saliva and coated the oropharyngeal surface. On average, the amount of the test substance was 2.5 to 3 mg per tablet.

To test for anti-nociceptive activity, the ODT containing the test compound was first administered onto the dorsal surface of the tongue; 45 to 50 minutes later, the chili-pepper sauce challenge is administered. At this time, the coolness sensations from the test compound have dissipated and the test is to determine if an anti-nociceptive effect remains. Results were reported as follow: If there was no attenuation of the challenge stimuli, the score was (0), if there was partial inhibition, the score was (+), and if there was complete attenuation of the irritant signal, the score was (++). In the presence of an ODT containing an active ingredient that results in a (++) score, the irritative signals were completely absent, yet the salty taste used in the soy sauce of the condiment could be readily identified and tasted.

Study 1

Data recorded for tests on keratinized stratified epithelium and non-keratinized stratified epithelium (NKSE) are summarized in the following table.

| # | Code | Keratinized Stratified Epithelia Philtrum Skin (min) [1] | Non-Keratinized Stratified Epithelia (NKSE) | |
|---|---|---|---|---|
| | | | Ocular Surface (min) [2] | Oropharyngeal Surface [3] |
| 1 | Gly-O—Me | 10 | 5 | 0 |
| 2 | Gly-O—Et | 24 | 15 | 0 |
| 3 | Gly-O—nPr | 42 | 54 | 0 |
| 4 | Gly-O—iPr | 27 | 300 | ++ |
| 5 | Gly-O—nBu | 38 | 35 | 0 |

[1] applied to the philtrum skin at 5 mg/mL in Aquaphor ® ointment.
[2] applied to the closed eyelids using a towellette at 1 mg/mL in 5%-95% v/v ethanol-distilled water.
[3] applied on the dorsal surface, at the back of the tongue, as an ODT containing 2.5 to 3 mg of the active ingredient; 45 minutes later, chili pepper sauce was applied to the tongue surface and the subjective sensations are recorded. When a (++) response was recorded, the irritative properties of the chili pepper sauce were no longer detected.

Gly-O-iPr has one of the shorter durations on keratinized epithelia, but by far the longest duration on non-keratinized epithelia. The super-prolonged effect of Gly-O-iPr on the ocular surface was both surprising and unexpected. The cooling effect lasted on average for 5 hours. Increasing the test concentration of Gly-O-iPr from 1 mg/mL to 1.5 mg/mL further increased the duration on the ocular surface to about 6.5 hours. By comparison, if the concentration of Gly-O-Et was increased from 1 mg/mL to 2 mg/mL or even to 5 mg/mL, the intensity of the cooling sensation was increased, but the duration was increased by only 15 to 22 minutes, respectively. The selective action of Gly-O-iPr on the non-keratinized ocular surfaces reflects a difference in the type of pharmacological activity, and is not simply a matter of administered dose.

Six subjects agreed to test the Gly-O-Et, Gly-O-iPr, and Gly-O-nPr ocular wipes in a randomized double-blind study, with three trials per wipe. The results were unequivocal and demonstrated a duration of action with Gly-O-iPr>>Gly-O-nPr>Gly-O-Et.

On the oropharyngeal surface, both Gly-O-iPr and Gly-O-Et exerted a refreshing cooling sensation. However, Gly-O-iPr produced a prolonged and lingering refreshing "feel" in the oral cavity which was not experienced with either Gly-O-Et or Gly-O-nPr, and which blocked the response to the chili pepper sauce. Gly-O-Et and Gly-O-nPr were not effective under the same test conditions.

Thus, Gly-O-iPr has surprising and unexpected properties which are distinct from those of Gly-O-Me, Gly-O-Et, Gly-O-nPr, and Gly-O-nBu.

Study 2

The Ames test (named after Prof. B. N. Ames of the University of California at Berkeley) is an assay performed in bacteria to determine the mutagenic potential of a test compound. If a positive result is obtained, then the test compound may interact with nucleic acids and be a risk to genetic materials. The Ames test is a standard tool in safety evaluation.

In the material safety data sheet for Gly-O-Et (MSDS Number 2984, 9 Nov. 2005, from SCM Europe SA/NV, 141 Rue St. Lambert Suite 2, B-1200, Brussels, Belgium), under the category of mutagenicity, it is noted that: "An Ames test yielded a weakly mutagenic result for [Gly-O-Et] in the TA1535 strain under the conditions of the test. The responses were small, and did show a degree of reproducibility."

Gly-O-iPr was evaluated for mutagenic activity in the *Salmonella typhimurium* tester strain TA1535 (Ames test for this strain) by Notox, BV, Hambakenwetering, PO Box 34763, Hertogenbosch, the Netherlands (a contract research organization that specializes in safety evaluation and testing). Gly-O-iPr was tested in TA1535 in the presence and absence of S9-mix (rat liver S9-mix induced by a combination of phenobarbital and β-naphthoflavone). Gly-O-iPr was provided as a white crystalline powder synthesized by Phoenix Pharmaceuticals, Inc. (Burlingame, Calif.) with a purity of ≧95% by weight, and was dissolved in dimethyl sulfoxide (DMSO).

Gly-O-iPr was tested at concentrations ranging from 3 to 5000 μg/plate, at eight dose-levels. Gly-O-iPr did not precipitate on the plates at the top dose of 5000 μg/plate. The bacterial background lawn was not reduced at any of the concentrations tested, and no biologically relevant decrease in the number of revertants was observed.

Gly-O-iPr did not induce a significant dose-related increase in the number of revertant (His$^+$) colonies in TA1535 in the absence and presence of S9-metabolic activation. In this study, the negative and strain-specific positive control values (induced by sodium azide or 2-aminoanthracene) were within the laboratory historical control data ranges indicating that the test conditions were adequate and that the metabolic activation system functioned properly. Based on the results of this study, it was concluded that Gly-O-iPr is not mutagenic in the *Salmonella typhimurium* tester strain TA1535.

Thus, Gly-O-iPr does not share the toxicological properties of Gly-O-Et. This result was surprising and unexpected, because the structures of these two compounds are closely related.

Study 3

A laboratory scientist suffered from seasonal allergic conjunctivitis. This condition was severely aggravated when he started doing experiments with laboratory animals (rats and mice) and he became sensitized to the associated allergens. The conjunctivitis was not relieved by oral or topical eye drops containing antihistamines and the subject was reluctant to consider the use of anti-inflammatory steroid ointments. Upon examination, his eyes were blood-shot and watery and he kept rubbing his eyelids with his fingers even though he knew this action may further aggravate the itch and discomfort. He volunteered to try eye wipes containing 1.0 mg/mL of Gly-O-iPr. The relief of itch and discomfort was obtained within 5 minutes and lasted for at least four hours. He used the wipes on an "as-needed basis" for three days and was surprised to see that his over-all itchiness and redness were reduced significantly.

Study 4

A 52-year old male's daughter moved away from his neighborhood to go to college and he became responsible for taking care of her two cats. Initially everything was all right, but then he became sensitized to the litter box dust generated when he was cleaning after the cats. He developed a dry, scratchy throat with cough, and this was severely aggravated by his seasonal allergy to grass pollen, so that he was constantly clearing his throat. Standard non-sedating antihistamines did not alleviate his irritated upper airways. After about two weeks of coughing and discomfort, he agreed to try Gly-O-iPr, first spread as 3 mg per wafer of Wrigley spearmint chewing gum, and then later formulated in an orally disintegrating tablet at 3 mg per unit dose. The medicated chewing gum and the ODT both provided relief within five minutes after administration. The sense of discomfort in the throat was attenuated and the effect lasted for about four hours and the dose could be repeated with the same beneficial effect. This individual preferred the ODT method of delivery as he considered this more efficient than chewing gum. After using the ODT containing Gly-O-iPr for ten days on an "as-needed basis" his cough and scratchy throat disappeared and he is now well.

Study 5

A 60-year old venture capitalist lived a stress-filled life and smoked two packs of cigarettes per day. He had a smoker's cough and he said his doctor had diagnosed him as being a borderline case of chronic obstructive pulmonary disease (COPD). He tried the ODT containing 2.5 mg of Gly-O-iPr and said that it felt great, but he was afraid that if he used it, he would smoke more. Later that evening, he went to a banquet of Northern Chinese cuisine and he started coughing when he ate a piece of fish that was heavily spiced with chili peppers. Everyone at the dinner table was alarmed by his coughing fit which was quite intense and made his face turn bright red. He immediately took two of the ODT tablets containing Gly-O-iPr and to everyone's amazement, the cough stopped within a few minutes.

Study 6

A 66-year old male developed adult onset asthma over the past ten years, which was aggravated by seasonal allergy to tree pollen. He was medicated with a bronchodilator inhaler and Singulair®, and also used antihistamines and inhaled steroids on an episodic basis. He coughed often and complained of tightness and discomfort in the area of his chest around the sternum. His doctor told him he was also considered a borderline case of chronic obstructive pulmonary disease because of his ventilation problems. He agreed to try an ODT containing 3 mg of Gly-O-iPr together with 12 mg of icilin formulated into a 180 mg tablet with mannitol as the excipient. After use of the first ODT containing Gly-O-iPr/icilin, he felt much better for the first 15 minutes, but a repeat dose resulted in relief of throat and airway discomfort which lasted for 10 hours. He felt he could move about more easily and with less discomfort. He continued the use of the ODT containing Gly-O-iPr/icilin for a week and noted that he coughed less, cleared his throat less often, and was able to sleep better.

Compositions

One aspect of the present invention pertains to a composition (e.g., a pharmaceutical composition) comprising an IPE compound, as described herein, and a pharmaceutically acceptable carrier, diluent, or excipient.

Another aspect of the present invention pertains to a method of preparing a composition (e.g., a pharmaceutical composition) comprising admixing an IPE compound, as described herein, and a pharmaceutically acceptable carrier, diluent, or excipient.

Certain Compositions

In one embodiment, the composition is in the form of a liquid (e.g., an aqueous liquid).

In one embodiment thereof, the compound is present in the composition at a concentration of 0.01 to 5% w/v.

In one embodiment, the composition is in the form of eye drop solution.

In one embodiment thereof, the compound is present in the composition at a concentration of 0.01 to 1% w/v.

In one embodiment, the composition is in the form of an ointment or cream.

In one embodiment thereof, the compound is present in the composition at a concentration of 0.5 to 5 mg/mL.

In one embodiment, the composition is in the form of a powder, a tablet, a lozenge, a pastille, a film, a paste, or a gum.

In one embodiment, the composition is in the form of a tablet.

In one embodiment, the composition is in the form of an orally disintegrating tablet (ODD.

In one embodiment, the composition is in the form of a sugar candy (e.g., a confection made from a concentrated solution of sugar in water, to which flavorings and colorants are added).

In one embodiment, the composition is in the form of a gum.

In one embodiment, the composition is in the form of chewing gum.

In one embodiment thereof, the compound is present in the composition at a concentration of 0.5 to 5% by weight.

Compositions Suitable for Topical Administration

In one embodiment, the composition is suitable for topical administration to a human.

In one embodiment, the composition is suitable for topical ocular administration to a human.

In one embodiment, the composition is suitable for topical ocular administration to the eyelid, the margin of the eyelid, the anterior part of the eyeball, the conjunctiva, the lachrymal system, the pre-corneal film or the cornea of a human.

In one embodiment, the composition is suitable for topical oral administration to a human.

In one embodiment, the composition is suitable for topical administration to the lining of the oral cavity of a human.

In one embodiment, the composition is suitable for topical administration to the internal portion of the lips of a human.

In one embodiment, the composition is suitable for topical pharyngeal administration to a human.

In one embodiment, the composition is suitable for topical administration to the pharyngeal surface of a human.

In one embodiment, the composition is suitable for topical esophageal administration to a human.

In one embodiment, the composition is suitable for topical administration to the esophageal surface of a human.

In one embodiment, the composition is suitable for topical anogenital administration to a human.

In one embodiment, the composition is suitable for topical administration to the anogenital surface of a human.

Wipes, Pads, and Towelettes

Another aspect of the invention is a wipe, pad, or towelette carrying an aqueous composition comprising an IPE compound.

In one embodiment, the aqueous composition is water further comprising the compound.

In one embodiment, aqueous composition is an isotonic saline solution further comprising the compound.

In one embodiment, the compound is present in the aqueous composition at a concentration of 0.01 to 1% w/v.

In one embodiment, the aqueous composition further comprises an adjunctive ocular drug.

In one embodiment, the adjunctive ocular drug is a polymer lubricant, hypromellose, polyethylene glycol 400, hyaluronan, or propanediol.

In one embodiment, the wipe, pad, or towelette is suitable for use in the topical administration of the compound to a human.

In one embodiment, the wipe, pad, or towelette is suitable for use in the topical ocular administration of the compound to a human.

In one embodiment, the wipe, pad, or towelette is suitable for use in the topical ocular administration of the compound to the eyelid, the margin of the eyelid, the anterior part of the eyeball, the conjunctiva, the lachrymal system, the pre-corneal film or the cornea of a human.

For example, an eye wipe with a single cooling agent (e.g., Gly-O-iPr) as the active pharmacological ingredient (API) may be used as a stand alone analgesic wipe. Alternatively, the API may be combined with other agents in the wipe in order to improve therapy. Examples of such adjunctive ocular drugs are demulcents such as polymer "lubricants", hypromellose, polyethylene glycol 400, hyaluronan, and propanediol(s). The lubricants increase the elastoviscous properties of the ocular fluids (usually this can be achieved with ophthalmic solutions in the range of 25 to 50 centipoises) and are especially useful for the dry eyes syndrome.

Uses

The IPE compounds, as described herein, are useful, for example, in the treatment of sensory discomfort in a human, as described herein.

Use in Methods of Therapy

Another aspect of the present invention pertains to an IPE compound, as described herein, for use in a method of treatment of the human or animal body by therapy.

Use in the Manufacture of Medicaments

Another aspect of the present invention pertains to use of an IPE compound, as described herein, in the manufacture of a medicament for use in treatment.

In one embodiment, the medicament comprises the IPE compound.

Methods of Treatment

Another aspect of the present invention pertains to a method of treatment comprising administering to a patient in need of treatment a therapeutically effective amount of an IPE compound, as described herein, preferably in the form of a pharmaceutical composition.

Indications

In one embodiment (e.g., of use in methods of therapy, of use in the manufacture of medicaments, of methods of treatment), the treatment is treatment or prevention of sensory discomfort of non-keratinized stratified epithelial (NKSE) tissue.

As used herein, the term non-keratinized stratified epithelial (NKSE) tissue is intended to refer to tissue comprising (e.g., primarily comprising) non-keratinized stratified epithelial (NKSE) cells. Examples of NKSE tissue are ocular surfaces including the margin of the eyelid, the anterior part of the eyeball, the conjunctiva, the lachrymal system, the pre-corneal film, and the cornea; the lining of the oral cavity including the internal portion of the lips; the pharyngeal surface; the esophageal surface; and the anogenital surface.

In one embodiment (e.g., of use in methods of therapy, of use in the manufacture of medicaments, of methods of treatment), the treatment is treatment or prevention of one or more of the following:

sensory discomfort of an eyelid, a margin of an eyelid, an anterior part of an eyeball, a conjunctiva, a lachrymal system, a pre-corneal film, or a cornea;

sensory discomfort of a lining of the oral cavity, an internal portion of the lips, a pharyngeal surface, or an esophageal surface;

sensory discomfort of an anogenital surface;

eye discomfort;

eye discomfort caused by extended wear of contact lenses, eye discomfort caused by eye strain and/or fatigue, eye discomfort caused by air pollutants, or eye discomfort caused by excessive exposure to the sun;

eye discomfort caused by conjunctivitis;

eye discomfort caused by dry eye syndrome;

sensory discomfort associated with oral mucositis;

airway (e.g., larynx, trachea, and/or bronchi) tightness, discomfort in the airways (e.g., larynx, trachea, and/or bronchi), choking, cough, and/or dyspnea;

airway (e.g., larynx, trachea, and/or bronchi) tightness and/or discomfort in the airways (e.g., larynx, trachea, and/or bronchi);

cough;

airway (e.g., larynx, trachea, and/or bronchi) tightness, discomfort in the airways (e.g., larynx, trachea, and/or bronchi), choking, cough, and/or dyspnea associated with asthma; and airway (e.g., larynx, trachea, and/or bronchi) tightness, discomfort in the airways (e.g., larynx, trachea, and/or bronchi), choking, cough, and/or dyspnea associated with chronic obstructive pulmonary diseases (COPD).

Indications: Ocular

The eye surfaces are exposed to the external environment. These anatomical structures—eyelids, front (anterior) part of the eyeball, conjunctiva, lachrymal system, pre-corneal film and cornea—are subject to injury by physical, chemical and biological agents. The results of injury to the eye surfaces are symptoms of discomfort, typically including blurring of vision, itching, irritation, fatigue in vision, a sense of dryness, burning sensations, and/or pain. The signs of injury in the eye are typically redness, swelling, and/or increased blood flow. Ophthalmic products such as solutions (e.g., eyedrops), ointments, and inserts are used to manage the symptoms and signs of eye injury.

An irritated eye surface is an especially common symptom of the condition known as "dry eyes", which is caused by decreased tear formation and exacerbated, for example, by a dry climate, an increased use of contact lenses, excessive staring at computer screens, and ageing. The estimated prevalence of dry eyes in the United States is about 10 to 30% of the population aged over 40, with about 4.9 million severe cases requiring specific medical treatment. There is need for improved treatment.

Additional Eye Disorders that Cause Eye Discomfort Include:

General eye discomfort: for example, caused by extended wear of contact lenses, by eye strain and/or fatigue, by air pollutants, or by excessive exposure to the sun.

Conjunctivitis: an inflammation of the conjunctiva that is most commonly caused by allergens, smoke, and/or pollutants, but which may also be caused by bacterial and viral infection, or by physical agents such as trauma, wind and sunlight.

Dry eye syndrome (keratoconjunctivitis sicca): the inadequate wetting of the ocular surface caused, for example, by inadequate tear secretion or rapid evaporation of tears because of poor tear quality.

Indications: Oral Cavity and Pharyngeal

The dorsal surface of the tongue is lined with keratinized epithelia. The oral cavity and pharyngeal surfaces are lined by non-keratinized stratified epithelium (NKSE). The pharynx is divided into three regions: naso, oro and laryngo. The oropharynx is an especially busy traffic zone as every day for the adult an average 12,000 L of air and 2 kg of food pass through, and it is essential for survival that the traffic flow is correct and food does not go into the airways. The swallow reflex and the cough reflex protect the airways against solid particles. The narrowest point of the traffic zone is called the lower retropalatal oropharynx (LRO) and has a cross-section of about 1 cm$^2$.

The sensations that lead to sensory discomfort of the oral cavity and pharyngeal surfaces are multi-factorial and include short-term conditions, such as infections, allergies, cancer chemotherapy, inflammation caused by pollutants, and chronic conditions, such as pharyngitis, laryngitis, asthma, chronic obstructive pulmonary disease (COPD), gastroesophageal reflux disease, lung cancer, pneumonia, pulmonary edema, and congestive heart failure.

The sensitivity of the oral cavity and pharyngeal surfaces to injury and pain is illustrated by the conditions known as oral mucositis (20 to 40% incidence) caused by cancer treatments such as radiotherapy and chemotherapy for head and neck cancer. Mucositis originates in the lining of the oral cavity/pharynx and results from toxic injury to epithelial stem cells that fail to rejuvenate and replace upper layers of cells normally lost by desquamation. Oral mucositis produces sensations of dryness; pain, especially upon eating and chewing; dysphagia; and loss of quality of life. The condition progresses over several weeks, and in ulcerated and infected forms, threatens life and interrupts treatment. Pain, a prominent symptom, is likely caused by inflammatory mediators and loss of epithelial cells down to the basement membrane, which then exposes the sensory nerve endings of the connective tissue stroma. Pain relief is attempted with mouthwashes containing local anesthetics, morphine, antihistamines, or soothing remedies such as honey. These agents have a limited duration of efficacy and undesired side-effects; for example, local anesthetics may interfere with the proper chewing of food.

The sensory nerve endings within the oral cavity/pharyngeal NKSE are on the topical or luminal surfaces of tissues and thus accessible to localized drug delivery.

Treatment

The term "treatment," as used herein in the context of treating a disorder, pertains generally to treatment and therapy, of a human, in which some desired therapeutic effect is achieved, for example, the inhibition of the progress of the disorder, and includes a reduction in the rate of progress, a halt in the rate of progress, alleviation of symptoms of the disorder, amelioration of the disorder, and cure of the disorder. Treatment as a prophylactic measure (i.e., prophylaxis) is also included. For example, use with patients who have not yet developed the disorder, but who are at risk of developing the disorder, is encompassed by the term "treatment."

For example, treatment includes the prophylaxis of eye discomfort, reducing the incidence of eye discomfort, alleviating the symptoms of eye discomfort, etc.

The term "therapeutically-effective amount," as used herein, pertains to that amount of a compound, or a material, composition or dosage form comprising a compound, which is effective for producing some desired therapeutic effect, commensurate with a reasonable benefit/risk ratio, when administered in accordance with a desired treatment regimen.

Combination Therapies

The term "treatment" includes combination treatments and therapies, in which two or more treatments or therapies are combined, for example, sequentially or simultaneously. For example, the compounds described herein may also be used in combination therapies, e.g., in conjunction with other agents.

One aspect of the present invention pertains to a compound as described herein, in combination with one or more (e.g., 1, 2, 3, 4, etc.) additional therapeutic agents.

The particular combination would be at the discretion of the physician who would select dosages using his common general knowledge and dosing regimens known to a skilled practitioner.

The agents (i.e., the compound described herein, plus one or more other agents) may be administered simultaneously or sequentially, and may be administered in individually varying dose schedules and via different routes. For example, when administered sequentially, the agents can be administered at closely spaced intervals (e.g., over a period of 5-10 minutes) or at longer intervals (e.g., 1, 2, 3, 4 or more hours apart, or even longer periods apart where required), the precise dosage regimen being commensurate with the properties of the therapeutic agent(s).

The agents (i.e., the compound described here, plus one or more other agents) may be formulated together in a single dosage form, or alternatively, the individual agents may be formulated separately and presented together in the form of a kit, optionally with instructions for their use.

Pharyngeal and Esophageal Applications

Localized delivery of TRP-M8 agonists to pharyngeal and esophageal sites may have benefit in relieving symptoms of airway tightness, choking, cough, and dyspnea in conditions such as asthma and/or chronic obstructive pulmonary diseases (COPD). This mechanism of action is indirect and is based on the convergence of sensory inputs from the upper gastrointestinal tract (pharynx and esophagus) and from afferents in the upper airways (larynx, trachea and bronchi) in the brainstem. These sensory inputs come from two cranial nerves, the glossopharyngeal ($9^{th}$ nerve) and the vagus ($10^{th}$). Thus, delivery of a TRP-M8 agonist onto the oropharyngeal and esophageal surface will send, via the glossopharyngeal/vagus nerves, a signal into the brainstem that will indirectly "gate" the nociceptive signals from the vagus and thus achieve the therapeutic goals of reducing cough and airway irritation.

The inventor has determined, experimentally, that Gly-O-iPr formulated together with icilin (a known TRP-M8 agonist), has the desired property of causing mild cooling sensations in the chest extending down to the xyphoid process, most likely because of action on pharyngeal and esophageal receptors. Gly-O-iPr alone is less effective because its actions remain localized in the oropharynx. The cooling sensations in the chest that result from the Gly-O-iPr/icilin combination may provide symptomatic relief of discomfort in the airways (larynx, trachea, bronchi) in conditions such as asthma and COPD.

Thus, in one embodiment, the additional therapeutic agent is icilin. For example, in one embodiment, the present invention pertains to a compound as described herein, in combination with icilin.

Kits

One aspect of the invention pertains to a kit comprising (a) an IPE compound as described herein, or a composition comprising an IPE compound as described herein, e.g., preferably provided in a suitable container and/or with suitable packaging; and (b) instructions for use, e.g., written instructions on how to administer the compound or composition.

The written instructions may also include a list of indications for which the active ingredient is a suitable treatment.

Route of Administration

The IPE compound or pharmaceutical composition comprising the IPE compound is administered to a subject topically (i.e., at the site of desired action).

In one embodiment, the administration is topical administration to a human.

In one embodiment, the administration is topical ocular administration to a human.

In one embodiment, the administration is topical ocular administration to the eyelid, the margin of the eyelid, the anterior part of the eyeball, the conjunctiva, the lachrymal system, the pre-corneal film or the cornea of a human.

In one embodiment, the administration is topical oral administration to a human.

In one embodiment, the administration is topical administration to the lining of the oral cavity of a human.

In one embodiment, the administration is topical administration to the internal portion of the lips of a human.

In one embodiment, the administration is topical pharyngeal administration to a human.

In one embodiment, the administration is topical administration to the pharyngeal surface of a human.

In one embodiment, the administration is topical esophageal administration to a human.

In one embodiment, the administration is topical administration to the esophageal surface of a human.

In one embodiment, the administration is topical anogenital administration to a human.

In one embodiment, the administration is topical administration to the anogenital surface of a human.

The Subject/Patient

In one embodiment, the subject/patient is a human.

Formulations

While it is possible for the IPE compound to be administered alone, it is preferable to present it as a pharmaceutical formulation (e.g., composition, preparation, medicament) comprising at least one IPE compound, as described herein, together with one or more other pharmaceutically acceptable ingredients well known to those skilled in the art, including, but not limited to, pharmaceutically acceptable carriers, diluents, excipients, adjuvants, fillers, buffers, preservatives, anti-oxidants, lubricants, stabilisers, solubilisers, surfactants (e.g., wetting agents), masking agents, colouring agents, flavouring agents, and sweetening agents. The formulation may further comprise other active agents, for example, other therapeutic or prophylactic agents.

Thus, the present invention further provides pharmaceutical compositions, as defined above; and methods of making a pharmaceutical composition comprising admixing at least one IPE compound, as described herein, together with one or more other pharmaceutically acceptable ingredients well known to those skilled in the art, e.g., carriers, diluents, excipients, etc. If formulated as discrete units (e.g., tablets, etc.), each unit contains a predetermined amount (dosage) of the compound.

The term "pharmaceutically acceptable," as used herein, pertains to compounds, ingredients, materials, compositions, dosage forms, etc., which are, within the scope of sound medical judgment, suitable for use in contact with the tissues of the subject in question without excessive toxicity, irritation, allergic response, or other problem or complication, commensurate with a reasonable benefit/risk ratio. Each carrier, diluent, excipient, etc. must also be "acceptable" in the sense of being compatible with the other ingredients of the formulation.

Suitable carriers, diluents, excipients, etc. can be found in standard pharmaceutical texts, for example, *Remington's Pharmaceutical Sciences*, 18th edition, Mack Publishing Company, Easton, Pa., 1990; and *Handbook of Pharmaceutical Excipients*, 5th edition, 2005.

The formulations may be prepared by any methods well known in the art of pharmacy. Such methods include the step of bringing into association the compound with a carrier which constitutes one or more accessory ingredients. In general, the formulations are prepared by uniformly and intimately bringing into association the compound with carriers (e.g., liquid carriers, finely divided solid carrier, etc.), and then shaping the product, if necessary.

Formulations may suitably be in the form of liquids, solutions (e.g., aqueous, non-aqueous), suspensions (e.g., aqueous, non-aqueous), emulsions (e.g., oil-in-water, water-in-oil), elixirs, syrups, electuaries, mouthwashes, drops, tablets (including, e.g., coated tablets), granules, powders, lozenges, pastilles, capsules (including, e.g., hard and soft gelatin capsules), cachets, pills, gels, pastes, ointments, creams, lotions, oils, foams, sprays, mists, or aerosols.

Formulations suitable for topical oral administration include liquids, solutions (e.g., aqueous, non-aqueous), suspensions (e.g., aqueous, non-aqueous), emulsions (e.g., oil-in-water, water-in-oil), elixirs, syrups, electuaries, tablets, granules, powders, capsules, cachets, and pills.

Formulations suitable for topical oral (buccal) administration include mouthwashes, lozenges, pastilles, as well as patches, adhesive plasters, depots, and reservoirs. Lozenges typically comprise the compound in a flavored basis, usually sucrose and acacia or tragacanth. Pastilles typically comprise the compound in an inert matrix, such as gelatin and glycerin, or sucrose and acacia. Mouthwashes typically comprise the compound in a suitable liquid carrier.

Formulations suitable for topical oral (sublingual) administration include tablets, lozenges, pastilles, capsules, and pills.

Formulations suitable for topical oral (transmucosal) administration include liquids, solutions (e.g., aqueous, non-aqueous), suspensions (e.g., aqueous, non-aqueous), emulsions (e.g., oil-in-water, water-in-oil), mouthwashes, lozenges, pastilles, as well as patches, adhesive plasters, depots, and reservoirs.

Formulations suitable for topical (non-oral transmucosal) administration include liquids, solutions (e.g., aqueous, non-aqueous), suspensions (e.g., aqueous, non-aqueous), emulsions (e.g., oil-in-water, water-in-oil), gels, pastes, ointments, creams, lotions, oils, as well as patches, adhesive plasters, depots, and reservoirs.

Formulations suitable for topical (transdermal) administration include gels, pastes, ointments, creams, lotions, and oils, as well as patches, adhesive plasters, bandages, dressings, depots, and reservoirs.

Tablets may be made by conventional means, e.g., compression or moulding, optionally with one or more accessory ingredients. Compressed tablets may be prepared by compressing in a suitable machine the compound in a free-flowing form such as a powder or granules, optionally mixed with one or more binders (e.g., povidone, gelatin, acacia, sorbitol, tragacanth, hydroxypropylmethyl cellulose); fillers or diluents (e.g., lactose, microcrystalline cellulose, calcium hydrogen phosphate); lubricants (e.g., magnesium stearate, talc, silica); disintegrants (e.g., sodium starch glycolate, cross-linked povidone, cross-linked sodium carboxymethyl cellulose); surface-active or dispersing or wetting agents (e.g., sodium lauryl sulfate); preservatives (e.g., methyl p-hydroxybenzoate, propyl p-hydroxybenzoate, sorbic acid); flavours, flavour enhancing agents, and sweeteners. Moulded tablets may be made by moulding in a suitable machine a mixture of the powdered compound moistened with an inert liquid diluent.

Ointments are typically prepared from the compound and a paraffinic or a water-miscible ointment base.

Creams are typically prepared from the compound and an oil-in-water cream base. If desired, the aqueous phase of the cream base may include, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof.

Emulsions are typically prepared from the compound and an oily phase, which may optionally comprise merely an emulsifier or it may comprise a mixture of at least one emulsifier with a fat or an oil or with both a fat and an oil. Preferably, a hydrophilic emulsifier is included together with a lipophilic emulsifier which acts as a stabiliser. It is also preferred to include both an oil and a fat. Together, the emulsifier(s) with or without stabiliser(s) make up the so-called emulsifying wax, and the wax together with the oil and/or fat make up the so-called emulsifying ointment base which forms the oily dispersed phase of the cream formulations.

Suitable emulsifiers and emulsion stabilisers include Tween 60, Span 80, cetostearyl alcohol, myristyl alcohol, glyceryl monostearate and sodium lauryl sulfate. The choice of suitable oils or fats for the formulation is based on achieving the desired cosmetic properties, since the solubility of the compound in most oils likely to be used in pharmaceutical emulsion formulations may be very low. Thus the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for topical (intranasal) administration, where the carrier is a liquid, include, for example, nasal spray, nasal drops, or by aerosol administration by nebuliser, include aqueous or oily solutions of the compound.

Formulations suitable for topical (intranasal) administration, where the carrier is a solid, include, for example, those presented as a coarse powder having a particle size, for example, in the range of about 20 to about 500 microns which is administered in the manner in which snuff is taken, i.e., by rapid inhalation through the nasal passage from a container of the powder held close up to the nose.

Formulations suitable for topical (pulmonary) administration (e.g., by inhalation or insufflation therapy) include those presented as an aerosol spray from a pressurised pack, with the use of a suitable propellant, such as dichlorodifluoromethane, trichlorofluoromethane, dichoro-tetrafluoroethane, carbon dioxide, or other suitable gases.

Formulations suitable for topical (ocular) administration include eye drops wherein the compound is dissolved or suspended in a suitable carrier, especially an aqueous solvent for the compound.

Suitable formulations for the oral cavity and oropharynx include, for example, compositions such as liquids, powders, tablets, films, or pastes. Orally disintegrating tablets (ODD, as contemplated herein, are pharmaceutical dosage forms that disintegrate in saliva within 30 seconds of topical application on the surface of the tongue. A typical ODT is composed predominantly of an inert vehicle, diluent, or carrier. A medicinal agent (e.g., Gly-O-iPr) is interspersed within this carrier. The ODT will dissolve when placed on the dorsal surface of the tongue thereby releasing the medicinal agent so that it may come in contact with the tissues of the lower oropharynx (LRO). A typical diluent, carrier, or vehicle may be a "polyhydric alcohol" construed as describing the following substances: xylitol, mannitol, sorbitol, maltitol, isomaltitol, maltotriitol, lactitol, and β-linked-glucopyranasido-sorbitol. Flavoring agents such as the sweeteners, aspartame, sucralose, or alitame, may be added to mask any tastes. Typically, the mix is granulated to a uniformly dispersed blend; dispersing agents, anti-caking agents, and/or lubricants may be added; and the mixture is then compressed to form the ODT.

In one formulation (used in the biological evaluation studies described herein), orally disintegrating tablets (ODTs) were prepared using an 80:20 by weight mixture of mannitol-maltitol (Pearlitol™ and Sweetpearl™, Roquette Freres, France). This carrier has the advantage of completely masking bitter tastes that might be present in some of the test compounds. The test compound was first mixed with the mannitol-maltitol using a mortar and pestle, and then suspended in an equal volume of 10:90 v/v ethanol-distilled water. A disposable pipette was then used to aliquot the liquid mixture onto a sheet of wax paper and dried at room temperature. The dried tablets were then weighed and sorted. It was found by experiment that an 80 mg tablet containing 2 to 3 mg of test compound dissolved within 15 seconds when placed on the dorsal surface of the tongue and provided a good test dose.

The invention claimed is:

1. A method of selectively relieving sensory discomfort of the lining of the oral cavity, an internal portion of the lips, a pharyngeal surface, or an esophageal surface of a human comprising:

administering [((1R,2S,5R)-2-isopropyl-5-methyl-cyclohexanecarbonyl)-amino]-acetic acid isopropyl ester in a pharmaceutically acceptable carrier, diluent or excipient to said lining, internal portion or surface.

2. The method as in claim 1 wherein the administering of [((1R,2S,5R)-2-isopropyl-5-methyl-cyclohexanecarbonyl)-amino]-acetic acid isopropyl ester is in the form of a powder, a tablet, a lozenge, a pastille, a film, a paste, a candy, or a gum.

3. The method as in claim 2 wherein the administering of [((1R,2S,5R)-2-isopropyl-5-methyl-cyclohexanecarbonyl)-amino]-acetic acid isopropyl ester is in the form of an orally disintegrating tablet (ODT).

4. The method as in claim 3 wherein [((1R,2S,5R)-2-isopropyl-5-methyl-cyclohexanecarbonyl)-amino]-acetic acid isopropyl ester is present in the carrier, diluent or excipient at a concentration of 0.5 to 5% by weight or at a concentration of 0.01 to 5% w/v.

* * * * *